US008148112B2

(12) United States Patent
Nishimura et al.

(10) Patent No.: US 8,148,112 B2
(45) Date of Patent: Apr. 3, 2012

(54) SUGAR CHAIN CONTAINING 4-POSITION HALOGENATED GALACTOSE AND APPLICATION THEREOF

(75) Inventors: Shin-Ichiro Nishimura, Sapporo (JP); Noriko Nagahori, Sapporo (JP); Tomoki Hamamoto, Choshi (JP); Kiyoshi Okuyama, Choshi (JP); Toshitada Noguchi, Choshi (JP)

(73) Assignees: National University Corporation Hokkaido University, Sapporo-shi (JP); Yamasa Corporation, Choshi-shi (JP)

( * ) Notice: Subject to any disclaimer, the term of this patent is extended or adjusted under 35 U.S.C. 154(b) by 1223 days.

(21) Appl. No.: 11/815,329

(22) PCT Filed: Feb. 14, 2006

(86) PCT No.: PCT/JP2006/302529
§ 371 (c)(1),
(2), (4) Date: Aug. 2, 2007

(87) PCT Pub. No.: WO2006/088017
PCT Pub. Date: Aug. 24, 2006

(65) Prior Publication Data
US 2009/0018327 A1 Jan. 15, 2009

(30) Foreign Application Priority Data
Feb. 16, 2005 (JP) ................ 2005-038751

(51) Int. Cl.
C12P 19/50 (2006.01)
C12P 19/52 (2006.01)
C12P 19/26 (2006.01)
C07H 15/00 (2006.01)
C07H 5/04 (2006.01)
C07H 5/06 (2006.01)
C08B 37/00 (2006.01)

(52) U.S. Cl. ............. 435/82; 435/83; 435/84; 536/18.4; 536/18.7

(58) Field of Classification Search .................. None
See application file for complete search history.

(56) References Cited

U.S. PATENT DOCUMENTS

| 4,549,013 | A | * | 10/1985 | Hough et al. | 536/122 |
| 5,059,428 | A | * | 10/1991 | Wong et al. | 426/3 |
| 5,977,349 | A | * | 11/1999 | Catani et al. | 536/124 |

FOREIGN PATENT DOCUMENTS

| EP | 0 073 093 A1 | * | 4/1982 |
| EP | 0 067 535 A1 | * | 5/1982 |
| EP | 0 313 234 A1 | * | 10/1988 |
| EP | 0 447 359 A1 | * | 3/1991 |
| JP | 58 29795 | | 3/1983 |
| WO | WO98/35974 A1 | * | 2/1998 |
| WO | 2006/034225 | | 3/2006 |

OTHER PUBLICATIONS

Xia et al., "Synthesis of Fluorine-Containing Core-2 Tetrasaccharides," Synlett, No. 9, pp. 1291-1294 (Nov. 7, 2003).*

Burton et al., "Preparation of Fluorinated Galactosyl Nucleoside Diphosphates to Study the Mechanism of the Enzyme Galactopyranose Mutase," J. Chem.Soc., Perk. Trans. I, Org. Bio-org. Chem., No. 16, pp. 2375-2382 (1997).*

Thoden et al., Structural Analysis of UDP-Sugar Binding to UDP-Galactose 4-Epimerase from *Escherichia coli*, Biochemistry, 36(21), 6294-6304 (1997).*

Van Dorst et al. (I), "Exploring the Substrate Specificities of a-2,6- and a-2,3-Sialyltransferases Using Synthetic Acceptor Analogues," European Journal of Biochemistry, 242(3), 674-681 (1996).*

Van Dorst et al. (II), "Synthesis of . . . , Probes for Substrate Specificity of Glycosyl Transferases: . . . ," Carbohydrate Research, 291, 63-83 (1996).*

Anon., Encyclopaedia Britannica (Online), definition of "oligosaccharide," obtained by a Google Search of the term "oligosaccharide" on Apr. 13, 2011.*

F. Feng et al. "Chemo-enzymatic synthesis of fluorinated 2-N-acetamidosugar nucleotides using UDP-GlcNAc pyrophosphorylase", Org. Biomol. Chem., vol. 2, pp. 1617-1623. (2004).

* cited by examiner

Primary Examiner — Lawrence E Crane
(74) Attorney, Agent, or Firm — Oblon, Spivak, McClelland, Maier & Neustadt, L.L.P.

(57) ABSTRACT

The present invention is directed to, for example, an oligosaccharide having at an end thereof a 4-position halogenated galactose residue represented by formula (I): (wherein

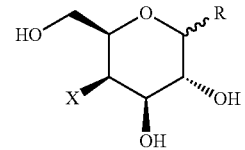

X represents a halogen atom, and R represents a monosaccharide, an oligosaccharide, or a carrier), a transferase inhibitor containing the oligosaccharide, and a method for inhibiting sugar chain elongation reaction in the presence of glycosyltransferase, the method including employing the inhibitor. The invention also provides a method for producing a 4-position halogenated galactose sugar nucleotide represented by formula (II):

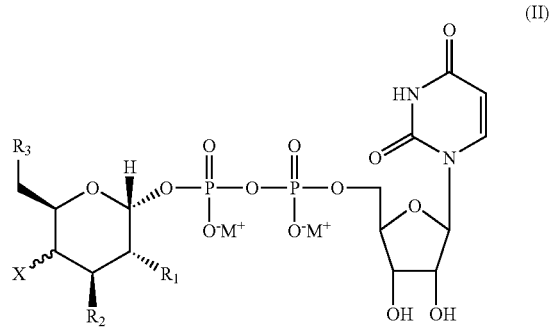

(wherein each of $R_1$ to $R_3$ represents a hydroxyl group, an acetyl group, a halogen atom, or a hydrogen atom; X represents a halogen atom; and M represents a hydrogen ion or a metal ion), wherein the method employs bacterium-derived galactokinase and bacterium-derived hexose-1-phosphate uridylyltransferase. The invention is also directed to a sugar chain containing 4-position halogenated galactose envisaged to be employed as drugs and other materials, and to applications of the compound.

14 Claims, No Drawings

SUGAR CHAIN CONTAINING 4-POSITION HALOGENATED GALACTOSE AND APPLICATION THEREOF

CROSS-REFERENCE TO RELATED APPLICATIONS

This application is a national-stage filing of PCT/JP06/302529, filed Feb. 14, 2006, which claims priority to Japan 2005 038751, filed Feb. 16, 2005.

TECHNICAL FIELD

The present invention relates to a sugar chain (oligosaccharide) containing 4-position halogenated galactose, which sugar chain is envisaged to be employed as drugs, etc., and to applications of the compound.

BACKGROUND ART

In vivo, sugar chains (oligosaccahrides) having a variety of structures are synthesized through successive bonding of sugar residues in a stereo-specific and regio-specific manner by the mediation of a sugar nucleotide serving as a sugar donor and glycosyltransferase. For example, in the case where certain cells undergo malignant alteration, in one conceivable mechanism, a new glycosyltransferase is expressed, or the balance of glycosyltransferases is varied, whereby a portion of the sugar chain structure is modified, and the sugar chain is elongated or modified, to form a tumor marker.

Thus, intentional modification of sugar chains present on cell surfaces is envisaged to change the nature and functions which the cells per se have, and many attempts have been extensively made to synthesize artificial, novel sugar chains in order to confirm the potential of the modified sugar chains.

In one means for synthesizing an artificial sugar chain, an artificial sugar nucleotide in which the structure of the sugar moiety has been modified is employed as a sugar donor in glycosyltransferase reaction, to thereby synthesize an artificial sugar chain.

One conceivable artificial sugar nucleotide is a sugar nucleotide whose hydroxyl groups have similar properties to those of a native sugar nucleotide and in which an inert halogen atom has been introduced. For example, the present inventors previously prepared fluorinated aminosugar nucleotides by introducing a fluorine atom to a hydroxyl group of N-acetylglucosamine and N-acetylgalactosamine, which are well known as essential compositional units of physiologically active sugar chains, and studied the properties of the products (Patent Document 1).

Similar to N-acetylglucosamine and N-acetylgalactosamine, regarding galactose, which is an essential component of a physiologically active sugar chain, a 4-position fluorinated galactose sugar nucleotide (Non-Patent Documents 1 and 2) and a galactose sugar nucleotide in which a fluorine atom has been introduced to a position other than the 4-position (Non-Patent Documents 3 to 5) were previously prepared.

Patent Document 1: JP-A-2004-168751
Non-Patent Document 1: J. Org. Chem., 59, 6994-6998 (1994)
Non-Patent Document 2: J. Chem. Soc., Perkin Trans. 1, 2375-2382 (1997)
Non-Patent Document 3: Bioorg. Med. Chem. 5, 497-500 (1997)
Non-Patent Document 4: Carbohydr. Res., 328, 473-480 (2000)
Non-Patent Document 5: Tetrahedron Letters. 34. (40), 6419-6422 (1993)

DISCLOSURE OF THE INVENTION

Problems to be Solved by the Invention

However, although the 4-position fluorinated galactose sugar nucleotide was chemically prepared, an artificial sugar chain has never been prepared from the fluorinated sugar nucleotide. Furthermore, fluorinated galactose sugar nucleotides in which the 2-, 3-, or 6-position of the galactose residue is fluorinated have been tested to evaluate applicability of the fluorinated sugar nucleotides to the synthesis of artificial sugar chains. Although the test revealed the applicability thereof to a sugar donor, no artificial sugar chain has ever actually been prepared.

Thus, even those skilled in the art could never be able to tell whether or not the 4-position fluorinated galactose sugar nucleotide, which is the most promising candidate for a sugar chain elongation inhibitor, can be employed as a sugar donor for the synthesis of an artificial sugar chain. Furthermore, granted that the 4-position fluorinated galactose sugar nucleotide can be employed as the sugar donor, those skilled in the art could never be able to tell whether or not the thus-prepared artificial sugar chain can serve as a transferase inhibitor.

Means for Solving the Problems

The present inventors have prepared a galactose sugar nucleotide in which a halogen atom has been introduced to the 4-position (i.e., 4-position hydroxyl group), which is a target site, and is conceived to be an important site in the sugar chain recognizing mechanism of a biomolecule, and which is a sole site stereochemically different from a stereoisomer, glucose. The inventors have also studied in detail on glycosyltransfer reaction when the artificial sugar nucleotide is employed as a sugar donor.

Specifically, if the 4-position halogenated galactose sugar nucleotide can function as a sugar donor in glycosyltransfer reaction in the presence of glycosyltransferase, (1) a sugar chain containing the halogenated sugar can serve as an inhibitor for subsequent sugar chain elongation, whereby there can be elucidated in vivo functions and roles of globo series Gb3 and Gb4, and ganglioside series GM2 (including glycolipids sequentially biosynthesized), which are sugar chains binding through 4-position of galactose and whose in vivo functions and roles have virtually not been elucidated; and (2) a variety of sugar chains which exhibit properties similar to those of sugar hydroxyl groups and which have an inert halogenated sugar can be synthesized, whereby in vivo functions and roles of sugar chains can be more clearly elucidated through comparison of a halogenated sugar containing sugar chain with the corresponding native sugar chain.

Through studies conducted by the present inventors, the following has been elucidated.

(a) Hitherto, galactose sugar nucleotides in which fluorine has been introduced to a position other than the 4-position have been prepared by use of two types of yeast-derived enzymes (galactokinase and galactose-1-phosphate uridylyltransferase). When the method is employed for the preparation of a 4-position fluorinated galactose sugar nucleotide, the yield is considerably low. Therefore, the inventors have conducted studies on enzymes other than yeast-derived enzymes, and have found that use of bacterium-derived enzymes; in particular, an *E. coli*-derived enzyme, realizes preparation of a target 4-position fluorinated galactose sugar nucleotide at high yield.

(b) Fluorinated aminosugar nucleotides which the present inventors previously prepared (e.g., uridine 5'-(2-acetamido-2,4-dideoxy-4-fluoro-α-D-glucopyranosyl) diphosphate and uridine 5'-(2-acetamido-2,4-dideoxy-4-fluoro-α-D-galactopyranosyl) diphosphate) cannot serve as a sugar donor in glycosyltransfer reaction by use of a transferase. The inventors have unexpectedly found that galactosyltransferase recognizes a 4-position fluorinated galactose sugar nucleotide as a sugar donor, whereby a variety of sugar chains containing 4-position fluorinated galactose can be readily synthesized.

(c) The inventors have found that sialyltransfer reaction by use of sialyltransferase with respect to sugar chain containing 4-position fluorinated galactose is inhibited.

The present inventors have accomplished the present invention on the basis of these findings.

Accordingly, the present invention provides an oligosaccharide having at an end thereof a 4-position halogenated galactose residue.

The invention also provides a method for producing an oligosaccharide having at an end thereof a 4-position halogenated galactose residue, characterized in that the method comprises transferring a 4-position halogenated galactose residue to a receptor sugar compound by glycosyltransferase using as a sugar donor a halogenated galactose sugar nucleotide represented by formula (II):

[F1]

(II)

(wherein each of $R_1$ to $R_3$ represents a hydroxyl group, an acetyl group, a halogen atom, or a hydrogen atom; X represents a halogen atom; and $M^+$ represents a hydrogen ion or a metal ion).

The present invention also provides a transferase inhibitor comprising an oligosaccharide having at an end thereof a 4-position halogenated galactose residue.

The present invention also provides a method for inhibiting sugar chain elongation reaction in the presence of glycosyltransferase, the method comprising employing as an inhibitor an oligosaccharide having at an end thereof a 4-position halogenated galactose residue.

The present invention also provides a method for producing a 4-position halogenated galactose sugar nucleotide, characterized in that the method comprises phosphorylating a compound represented by formula (III) by use of bacterium-derived galactokinase, to thereby form a compound represented by formula (IV), and synthesizing a compound represented by formula (II) from the compound represented by formula (IV) and a sugar nucleotide by use of bacterium-derived hexose-1-phosphate uridylyltransferase, the formulas being:

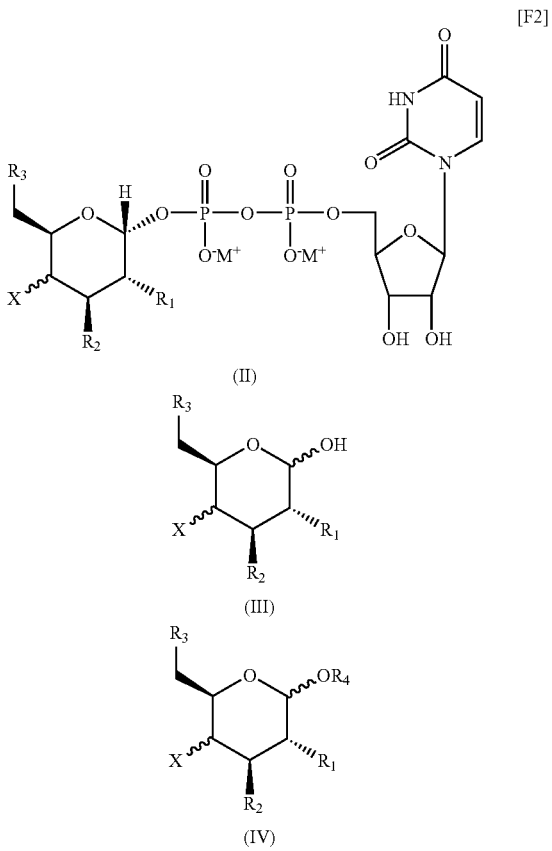

(wherein each of $R_1$ to $R_3$ represents a hydroxyl group, an acetyl group, a halogen atom, or a hydrogen atom; $R_4$ represents a phosphate residue or a salt thereof; X represents a halogen atom; and $M^+$ represents a hydrogen ion or a metal ion).

Effects of the Invention

The novel oligosaccharide of the present invention having at an end thereof a 4-position halogenated galactose residue (hereinafter may also be referred to as "oligosaccharide containing 4-position halogenated sugar") inhibits sugar chain elongation (biosynthesis route) in the presence of glycosyltransferase. Therefore, the oligosaccharide is envisaged to be developed so as to provide, for example, an inhibitor for inhibiting proliferation of cancer cells and viruses.

Inhibiting glycolipid elongation reaction (biosynthesis route) in a sugar chain binding through 4-position of galactose, specifically, globo series such as Gb3 and Gb4, and GM2 and thereafter in ganglioside series may elucidate functions and roles of the sugar chains, and at the same time applications of the sugar chain per se to functional materials, drugs, etc. are expected. In addition, it is reported that high sialylation of a sugar chain occurs when cells undergo malignant alteration. Therefore, application of the oligosaccharide of the invention is also promising in relation to an antitumor agent or a similar agent on the basis of the mechanism of sialyltransfer inhibition activity.

Furthermore, use of two bacterium-derived enzymes realizes high-yield mass-production of a 4-position halogenated galactose sugar nucleotide, which has been difficult to attain through chemical synthesis.

BEST MODES FOR CARRYING OUT THE INVENTION

Hereinafter, the present invention will be described in terms of (1) enzymatic synthesis of a 4-position halogenated galactose sugar nucleotide, (2) an oligosaccharide having a 4-position halogenated galactose residue, and (3) inhibition of sugar chain elongation reaction in the presence of glycosyltransferase, in this order.

(1) Enzymatic synthesis of 4-Position Halogenated Galactose Sugar Nucleotide

As mentioned above, a characteristic feature of the enzymatic synthesis of a 4-position halogenated galactose sugar nucleotide of the present invention resides in that a compound represented by the aforementioned formula (III) is phosphorylated by use of galactokinase, to thereby form a compound represented by the aforementioned formula (IV), and a compound represented by formula (II) is synthesized from the thus-formed compound represented by formula (IV) and a sugar nucleotide, by use of hexose-1-phosphate uridylyltransferase. The scheme is as follows:

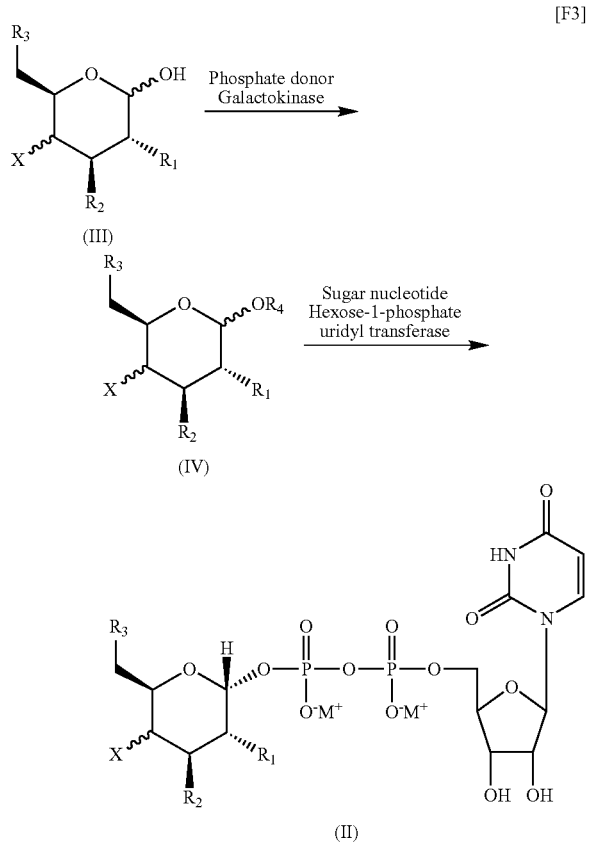

[F3]

(wherein $R_1$ to $R_4$, X, and M have the same meanings as defined above).

Examples of the halogen atom represented by each of $R_1$ to $R_3$ and X include a fluorine atom, a chlorine atom, a bromine atom, and an iodine atom, with a fluorine atom being preferred. Examples of the metal atom M include alkali metals such as sodium and potassium, and alkaline earth metals such as calcium and magnesium. In a particularly preferred compound represented by formula (II), each of $R_1$ to $R_3$ is a hydroxyl group, and X is a fluorine atom.

The compound represented by formula (III), which is a 4-position halogenated galactose and which serves as a starting material, is commercially available. Alternatively, the compound may be synthesized through a known method disclosed in, for example, Maradufu & Perlin, Carbohydr. Res., 32, 261-277 (1974), Ittah & Glaudemans, Carbohydr. Res., 95, 189-194 (1981), or Kamerling et al., Carbohydr. Res., 291, 63-83 (1996).

From the aforementioned materials, a compound (IV) is produced through phosphorylating in the presence of galactokinase.

The galactokinase employed in the reaction is preferably a bacterium-derived enzyme, with an *E. coli*-derived enzyme being particularly preferred. If the galactokinase gene has been cloned, the enzyme may be mass-produced through a routine method by use of the cloned galactokinase gene and a host such as *E. coli*, and the enzyme may be collected from the bacterial cells.

Bacterial cells may be collected by culturing a microorganism through a customary method in a culture medium capable of growing the microorganism, followed by collection of cells through centrifugation or a similar technique. Specifically, in the case where, for example, a bacterium belonging to the genus *Escherichia* is employed, there may be employed, as a culture medium, a bouillon medium, LB medium (1% trypton, 0.5% yeast extract, 1% sodium chloride), 2×YT medium (1.6% trypton, 1% yeast extract, 0.5% sodium chloride), or a similar medium. Microorganism cells may be collected through the following procedure. Specifically, seed cells are inoculated to such a culture medium, followed by culturing at about 30 to about 50° C. for about 10 to about 50 hours with optional stirring, and then the thus-cultured cells are separated through centrifugation from the culture broth.

The processed microorganism cells are treated through a generally employed technique, such as mechanical disruption (by a Waring blender, a French press, a homogenizer, a mortar, etc.), freeze-thawing, self-digestion, drying (freeze-drying, air-drying, etc.), treatment with an enzyme (e.g., lysozyme), ultrasonic treatment, or chemical treatment (acid treatment, alkali treatment, etc.), to thereby produce a disrupted product or a cell-wall-denatured or cell-membrane-denatured product of cells.

Examples of the enzyme product employed include a crude enzyme or purified enzyme prepared by subjecting, to a generally employed enzyme purification technique (e.g., salting-out, isoelectric precipitation, precipitation with an organic solvent, dialysis, or any chromatographic technique), a fraction exhibiting a target enzymatic activity obtained from the above processed cells. In order to prevent decomposition of a phosphate donor (i.e., nucleotide 5'-triphosphate (NTP) serving as a substrate) or sugar-1 phosphate serving as an intermediate and increase the product yield, an enzyme product free of residual dephosphorylation activity (phosphatase activity) is preferably employed.

In one embodiment of the phosphorylation by use of galactokinase, the compound represented by formula (III) (0.1 to 100 mM, preferably 1 to 50 mM) and nucleoside 5'-triphosphate (NTP) serving as a phosphate donor such as adenosine 5'-triphosphate (ATP) (1 to 500 mM, preferably 5 to 100 mM) are employed. In addition, 0.01 to 50 units/mL galactokinase is further added, and the mixture is incubated in a buffer (pH 4.0 to 10), at 10 to 70° C. for about 1 to about 100 hours.

Notably, NTP employed in the phosphorylation may be regenerated NTP which is produced through an NTP regeneration system in which polyphosphate kinase is acted on the nucleotide 5'-diphosphate (NDP) formed in the reaction (T. Noguchi & T. Shiba, Bioosci. Biotechnol. Biochem., 62, 1594-1596 (1998)), or a known NTP regeneration system in which pyruvate kinase is employed (C. H. Wong et al., J. Org. Chem., 57, 4343-4344 (1992)).

The compound represented by formula (II) is synthesized from the thus-produced compound represented by formula (IV) and a sugar nucleotide by use of hexose-1-phosphate uridylyltransferase.

No particular limitation is imposed on the sugar nucleotide employed in the reaction, so long as the sugar nucleotide serves as a substrate to the hexose-1-phosphate uridylyltransferase. Examples include uridine 5'-diphosphate glucose and uridine 5'-diphosphate galactose.

Similar to galactokinase, the hexose-1-phosphate uridylyltransferase employed in the reaction is preferably a bacterium-derived enzyme; in particular, an E. coli-derived enzyme. Such enzymes prepared through the aforementioned procedure may be employed.

In one embodiment of the transfer reaction in the presence of the hexose-1-phosphate uridylyltransferase, a compound represented by formula (IV) (0.1 to 100 mM, preferably 0.5 to 50 mM) and a sugar nucleotide (1 to 200 mM, preferably 5 to 100 mM) are employed, and 0.1 to 50 units/mL of a hexose-1-phosphate uridylyltransferase is added. The mixture is incubated in a buffer (pH 4.0 to 10.0), at 10 to 70° C. for about 1 to about 100 hours.

The sugar nucleotide applied to the transfer reaction may be a sugar nucleotide which is formed or regenerated through reacting glucose-1-phosphate with sugar nucleotide pyrophosphorylase in the presence of uridine 5'-triphosphate (UTP).

Phosphorylation in the presence of galactokinase and transfer reaction in the presence of hexose-1-phosphate uridylyltransferase may be performed sequentially or in parallel. A phosphorylated sugar formed through phosphorylation in the presence of galactokinase may be optionally purified for use in the transfer reaction.

The thus-produced 4-position halogenated galactose sugar nucleotide may be isolated and purified through a conventional means for isolation/purification of sugar nucleotides (e.g., ion-exchange chromatography, adsorption chromatography, or gel chromatography).

(2) Oligosaccharide having at an End Thereof a 4-Position Halogenated Galactose Residue The oligosaccharide having a 4-position halogenated sugar may be prepared through transferring a 4-deoxy-4-halogeno-galactosyl group to an acceptor compound by use of the aforementioned 4-position halogenated galactose sugar nucleotide as a sugar donor in the presence of glycosyltransferase.

No particular limitation is imposed on the transferase employed in the reaction, so long as the transferase can transfer a 4-deoxy-4-halogeno-galactosyl group. Specific examples include β1,4-galactosyltransferase, β1,3-galactosyltransferase, and α1,3-galactosyltransferase. No particular limitation is imposed on the origin of the transferase, and transferases of any origin such as animal-derived, plant-derived, and microorganism-derived transferases may be employed. When the gene of employed glycosyltransferase has been cloned, the glycosyltransferase may be prepared through a routine method by use of the cloned glycosyltransferase and a host such as E. Coli, yeast, insect cells, or animal cells.

The transferase may be in any form so long as the enzyme has an activity of interest. Examples of the form of enzyme include processed cell products and enzyme products produced from the cell products.

Examples of the processed cell products include a disrupted product or a cell-wall-denatured or cell-membrane-denatured product of cells produced through a generally employed technique, such as mechanical disruption (by a Waring blender, a French press, a homogenizer, a mortar, etc.), freeze-thawing, self-digestion, drying (freeze-drying, air-drying, etc.), treatment with an enzyme, ultrasonic treatment, or chemical treatment (acid treatment, alkali treatment, etc.).

Examples of the enzyme product employed include a crude enzyme or purified enzyme prepared by subjecting, to a generally employed enzyme purification technique (e.g., salting-out, isoelectric precipitation, precipitation with an organic solvent, dialysis, or any chromatographic technique), a fraction exhibiting a glycosyltransfer activity obtained from the above processed cells.

No particular limitation is imposed on the acceptor compound added to the reaction mixture, and the acceptor compound may be appropriately selected in accordance with the sugar chain to be synthesized or with the employed transferase from among known monosaccharides, oligosaccharides, and immobilized species in which a saccharide is bonded to a carrier via an optional spacer.

In one embodiment of the synthesis of an oligosaccharide having 4-position halogenated galactose, a 4-position halogenated galactose sugar nucleotide (0.1 to 100 mM) and a sugar compound serving as an acceptor (0.01 to 20 mM) are employed, and glycosyltransferase (0.001 units/mL or more, preferably 0.01 units/mL or more) is added. The mixture is allowed to react in a buffer (pH 5.0 to 10.0) such as Tris-HCl buffer or HEPES-NaOH buffer at 50° C. or lower, preferably about 5 to about 50° C. for about 1 to about 50 hours, with optional stirring in accordance with needs.

Examples of such oligosaccharides having 4-position halogenated galactose include 4-deoxy-4-halogeno-α-D-galactose derivatives represented by the following formula (I). The oligosaccharides may be synthesized from an acceptor (monosaccharide, oligosaccharide, or immobilized species thereof) with a 4-position halogenated galactose sugar nucleotide and galactosyltransferase.

[F4]

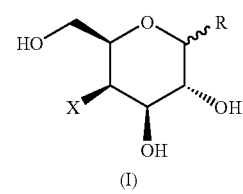

(I)

(wherein X represents a halogen atom, and R represents a monosaccharide, an oligosaccharide, or a carrier)

Examples of the compound represented by formula (I) include sugar chain derivatives having 4-deoxy-4-halogeno-α-D-galactosyl β1-4N-acetylglucosamine (compounds represented by the following formula (I')), and sugar chain derivatives having 4-deoxy-4-halogeno-α-D-galactosyl β1-3N-acetylglucosamine.

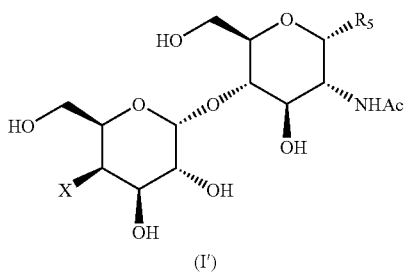

[F5]

(I')

(wherein X represents a halogen atom, and $R_5$ represents a hydrogen atom, a hydroxyl group, a monosaccharide, an oligosaccharide, or a carrier)

Examples of the halogen atom (X) include a fluorine atom, a chlorine atom, a bromine atom, and an iodine atom, with a fluorine atom being preferred. Examples of the monosaccharide (R or $R_5$) include galactose, glucose, mannose, fructose, ribose, arabinose, xylose, xylulose, ribulose, erythrose, threose, lyxose, allose, altrose, gulose, idose, talose, tagatose, sorbose, psicose, D-glycero-D-galacto-heptose, D-glycero-gluco-heptose, DL-glycero-D-manno-heptose, allo-heptulose, altro-heptulose, talo-heptulose, manno-heptulose, octulose, nonulose, D-glycero-L-galacto-octulose, D-glycero-D-mannno-octulose, nomulose, fucose, rhamnose, allomethylose, quinovose, antiallose, talomethylose, digitalose, digitoxose, cymarose, tyvelose, abelose, paratose, colitose, ascarylose, glucuronic acid, galacturonic acid, mannuronic acid, iduronic acid, glucronic acid, glucosamine, galactosamine, mannosamine, neuraminic acid, N-acetylglucosamine, N-acetylgalactosamine, N-acetylmannosamine, N-acetylneuraminic acid, N-acetyl-O-acetylneuraminic acid, N-glycolylneuraminic acid, muramic acid, and derivatives thereof.

Examples of the oligosaccharide include maltose, cellobiose, lactose, xylobiose, isomaltose, gentiobiose, melibiose, planteobiose, rutinose, primeverose, vicianose, nigerose, laminaribiose, turanose, kojibiose, sophorose, sucrose, trehalose, chitobiose, hyalobiouronic acid, chondrosine, cellobiouronic acid, raffinose, gentianose, melezitose, planteose, kestose, maltotriose, panose, isomaltotriose, stachyose, verbascose, cyclodextrin, starch, cellulose, chitin, chitosan, milk oligosaccharides (e.g., fucosyllactose, sialyllactose, lacto-N-tetraose, lacto-N-fucopentaose, and lacto-N-neotetraose), glycosaminoglycans such as hyaluronic acid, chondroitin sulfate, and dermatan sulfate, sugar chains depending on ABO blood type, N-bond sugar chains, mucin type (O-bond) sugar chains, glycolipid sugar chains such as sphingoglycolipid and glyceroglycolipid, and derivatives thereof.

Notably, the monosaccharide and oligosaccharide may be fluorescence-labeled. For example, the reducing end of monosaccharide or oligosaccharide may be labeled with benzamidine, p-methoxybenzamidine, 1,2-di-(p-methoxyphenyl)-ethylenediamine, Fmoc-hydrazine, ethyl-4-aminobenzene, 2-aminobenzoic acid, 2-aminopyridine, 2-aminoacridone, 8-aminonaphthalene-1,3,6-trisulfonic acid, 3-(acetylamino)-6-amminoacridine, 5-(dimethylamino)naphthalene-1-sulfonic acid, or a similar substance. Alternatively, an internal portion of an oligosugar chain may be labeled. Further, the Monosaccharides or oligosaccharides can be ones which are bonded to a compound which absorbs UV rays such as p-nitrophenol or a nucleotide base.

Examples of the carrier include biomaterials such as protein, lipid, and nucleic acid; microparticles of metals such as gold and platinum; microparticles of magnetic metals such as iron and iron oxide; and polymers such as polystryrene, polyacrylamide, agarose, and dextran. Examples of the spacer intervened between the carrier and the sugar chain include (poly)ethylene glycol and a variety of alkyl chains (e.g., C1 to C20 alkyls).

The thus-produced oligosaccharide derivatives having 4-position halogenated galactose may be isolated and purified through a conventional means for isolation/purification of oligosaccharide (e.g., ion-exchange chromatography, adsorption chromatography, or gel chromatography).

(3) Inhibition of Sugar Chain Elongation Reaction by Glycosyltransferase

Since the oligosaccharide having 4-position halogenated galactose, in particular the oligosaccharide having 4-position fluorinated galactose has a halogen atom (in particular a fluorine atom) which is bonded to the 4-position of galactose, the oligosaccharide can stop elongation of a sugar chain in which a sugar is bonded to the 4-position of galactose, or can remarkably retard elongation of the sugar chain. Thus, the oligosaccharide serves as a useful transferase inhibitor.

In addition, since a fluorine atom is bonded to the 4-position, transfer reaction in the presence of glycosyltransferase for bonding a sugar to, for example, the 3-position can also be inhibited. Through this mechanism, further biosynthesis of sugar chain may be inhibited. Therefore, the oligosaccharide is a promising inhibitor, and application thereof in the medicinal field is fully expected. Specifically, addition of a sugar chain having 4-position fluorinated galactose to the reaction system can inhibit the following transfer reactions: sialyl-transfer reaction by α2,3-sialyltransferase or α2,6-sialyltransferase; N-acetylglucosamine transfer reaction by β1,3-N-acetylglucosaminyltransferase; N-acetylgalactosamine transfer reaction by β1,3-N-acetylgalactosaminyltransferase; galactose transfer reaction by α1,3-galactosyltransferase; and N-acetylgalactosamine transfer reaction by α1,3-N-acetylgalactosaminyltransferase.

EXAMPLES

The present invention will next be described in detail by way of examples, which should not be construed as limiting the invention thereto.

4-Position fluorinated galactose in a reaction mixture was quantitated by means of an apparatus DX-300 (product of Dionex) with a PA1 column (CarboPac™) by use of an eluent; i.e., a mixture of distilled water (liquid A), 0.2M sodium hydroxide (liquid B), and 1M aqueous sodium acetate (liquid C). Nucleic acid-related substances such as uridine 5'-diphosphate 4-fluorogalactose (UDP-4F-Gal) in a reaction mixture was quantitated through the HPLC method. Specifically, separation was performed by means of an ODS-HS302 column (product of YMC) by use of a 0.2M triethylamine-phosphoric acid solution (pH 6.0) serving as an eluent.

Example 1

Synthesis of uridine 5'-diphosphate 4-fluorogalactose (1) Preparation of *E. coli*-Derived galactokinase (GalK)

*E. coli* (JM109 strain) (from Takara Bio) was transformed with a pTrc-galK plasmid (JP-A-2002-335988) in which a gene encoding *E. coli*-derived GalK has been inserted. The transformed cells were inoculated to a 2×YT medium (100 mL) containing 100 μg/mL ampicillin, followed by shake culturing at 37° C. When the number of the cells reached 1×10⁸ cells/mL, isopropyl-p-thiogalactoside (IPTG) was added to the culture so as to adjust the final concentration to 0.2 mM, and shake culture was continued for further eight hours. After completion of culturing, cells were collected through centrifugation (9,000×g, 20 min) and suspended in a buffer (20 mM Tris-HCl (pH 7.5) and 1 mM magnesium chloride) (10 mL). The cells were disrupted through ultrasonication, and the product was centrifuged (20,000×g, 10 min), to thereby remove cell residues.

The thus-produced supernatant fraction was dialyzed against the aforementioned buffer (total volume: 1 L), and purified by means of a HiTrapQ 5 mL column (product of Amersham Bioscience) under the conditions (liquid A; the above buffer, liquid B; liquid A+1M sodium chloride (5 to 35% liquid B) (20CV)), to thereby collect a fraction (15 mL) exhibiting galactokinase activity.

The thus-produced fraction was employed as an enzyme liquid in the following synthesis reactions. The galactokinase (GalK) activity of the enzyme liquid was determined (Table 1). In the present invention, GalK activity was determined through a method by Takeda et al. (JP-A-2002-335988).

(2) Preparation of *E. coli*-Derived galactose-1-phosphate uridylyltransferase (GalT)

*E. coli* (JM109 strain) (from Takara Bio) was transformed with a pTrc-GalT plasmid (JP-A-2002-335988) in which a gene encoding *E. coli*-derived GalT has been inserted. The transformed cells were inoculated to a 2×YT medium (50 mL) containing 100 μg/mL ampicillin, followed by shake culturing at 37° C. When the number of the cells reached 1×10$^8$ cells/mL, IPTG was added to the culture so as to adjust the final concentration to 1 mM, and shake culture was continued for further five hours. After completion of culturing, cells were collected through centrifugation (9,000×g, 20 min) and suspended in a buffer (50 mM HEPES-NaOH (pH: 8.0), 0.1 mM zinc sulfate, 10 mM 2-mercaptoethanol, and 50 mM sodium chloride) mL). The cells were disrupted through ultrasonication, and the product was centrifuged (20,000×g, 10 min), to thereby remove cell residues.

The thus-produced supernatant fraction was dialyzed against the aforementioned buffer (total volume: 1 L), and purified by means of a HiTrapQ 5 mL column (product of Amersham Bioscience) under the conditions (liquid A; the above buffer, liquid B; liquid A+1M sodium chloride (0 to 50% liquid B) (25CV)), to thereby collect a fraction (5 mL) exhibiting GalT activity.

The thus-produced fraction was employed as an enzyme liquid in the following synthesis reactions. The galactose-1-phosphate uridylyltransferase (GalT) activity of the enzyme liquid was determined (Table 1). In the present invention, GalT activity was determined through a method by Takeda et al. (JP-A-2002-335988). The thus-yielded galactose-1-phosphate uridylyltransferase is identical to hexose-1-phosphate uridylyltransferase and catalyzes the same reaction (E.C.2.7.7.12).

TABLE 1

| Enzyme | Enzymatic activity (units/mg protein) |
|---|---|
| GalK | 23.1 |
| GalT | 46.7 |

(3) Synthesis of 4-Position fluorinated galactose-1-phosphate (Gal-1P)

To a 100 mM Tris-HCl buffer (pH 7.8) containing 10 mM 4F-Gal (from Toronto Research Chemicals Inc.), 5 mM magnesium chloride, and 10 mM ATP, the enzyme liquid (2.3 units/mL-reaction mixture) prepared in (1) above and exhibiting galactokinase activity was added. The mixture was allowed to react at 37° C. for one hour. A similar system containing no 4F-Gal was also allowed to react as a control reaction.

A ¹⁄₁₀ volume of sodium hydroxide was added to the reaction mixture, and the resultant mixture was centrifuged (20,000×G, 10 minutes), to thereby remove insoluble fractions. The supernatant was analyzed by means of an ESI-ion trap mass analyzer (product of Hitachi High Technology). Analysis detected an [M–H]$^-$ peak (m/z 261), which had not been detected in the control reaction solution, thereby confirming that 4F-Gal-1P had been formed. Through analysis by means of Dionex DX-300, a decrease in 4F-Gal by 2.1 mM with respect to the control was determined, indicating that 2.1 mM of 4F-Gal-1P had been formed.

The aforementioned reaction mixture was applied to a DEAE-Toyopearl resin column (product of Tosoh)(gradient elution with ammonium chloride) and Sephadex G-10 (product of Amersham Bioscience) and eluted by use of 10 mM ammonium bicarbonate, to thereby isolate 4F-Gal-1P. Through lyophilization of the collected fraction, a white powder was yielded, which was employed in the following UDP-4F-Gal synthesis reaction.

(4) Synthesis of UDP-4F-Gal

To a 100 mM Tris-HCl buffer (pH 8.0) containing 10 mM 4F-Gal-1P, 5 mM magnesium chloride, and 20 mM uridine 5'-diphosphate glucose (UDP-Glc), the enzyme liquid (11 units/mL-reaction mixture) prepared in (2) above and exhibiting galactose-1-phosphate uridylyltransferase activity was added. The mixture was allowed to react at 37° C. for 22 hours.

The reaction mixture was treated at 90° C. for five minutes and, subsequently, centrifuged (20,000×g, 10 min), to thereby remove insoluble fractions. Through HPLC analysis of the thus-collected supernatant fraction, synthesis of UDP-4F-Gal (2.06 mM) was confirmed.

The supernatant fraction was further subjected to HPLC, to thereby collect a target peak fraction. After lyophylization of the fraction, the product was dissolved in distilled water, and the solution was subjected to gel filtration by means of a Sephadex G-10 resin column by use of 10 mM ammonium carbonate serving as a developer. The yielded UDP-4F-Gal fraction was lyophilized, to thereby produce UDP-4F-Gal (HPLC purity: 98%) as white powder.

$^1$H-NMR (600 MHz-D$_2$O)$_6$: 7.84 (1H, d, J=8.30 Hz, uri-H"-6), 5.87 (1H, d, J=4.76 Hz, rib-H'-1), 5.86 (1H, d, J=8.30 Hz, uri-H"-5), 5.56 (1H, dd, J=3.48, 7.29 Hz, H-1), 4.83 (1H, dd, J=2.34, 50.69 Hz, H-4), 4.28-4.25 (2H, m, rib-H'-2, 3), 4.18-4.07 (4H, m, rib-H'-4, 5S, 5R, H-5), 3.92 (1H, ddd, J=2.34, 10.31, 29.70 Hz, H-3), 3.76 (1H, dt, J=10.31, 3.48 Hz, H-2), 3.68-3.66 (2H, m, H-6a, 6b)

Referential Example 1

Synthesis of UDP-4F-Gal by use of Yeast-Derived galactose-1-phosphate uridylyltransferase To a 100 mM Tris-HCl buffer (pH 8.7) containing 10 mM 4F-Gal-1P, 5 mM magnesium chloride, and 20 mM uridine 5'-diphosphate glucose (UDP-Glc), yeast-derived galactose-1-phosphate uridylyltransferase (product of Sigma) (20 units/mL-reaction mixture) was added, and the resultant mixture was allowed to react at 25° C. for 36 hours.

The reaction mixture was treated at 90° C. for five minutes and, subsequently, centrifuged (20,000×G, 10 min), to thereby remove insoluble fractions. Through HPLC analysis of the thus-yielded supernatant fraction, formation of 0.61 mM of UDP-4F-Gal was confirmed. However, the amount of the target product was found to be very low; i.e., 30% or lower the amount of the same compound produced through the method of the present invention employing *E. coli*-derived galactose-1-phosphate uridylyltransferase.

Example 2

Synthesis of a sugar chain containing 4F-galactose by use of β1,4-galactosyltransferase N-acetylglucosamine (GlcNAc) immobilized on gold microparticles by the mediation of a thiol-group-containing spacer (see Referential Example 2) was employed as an acceptor (Compound 1). Human-derived β1,4-galactosyltransferase (product of Toyobo) (80 munits/mL-reaction mixture) was added to a 10 mM HEPES-NaOH buffer (pH 7.5) containing about 50 μM (as GlcNAc) the acceptor, 100 mM sodium chloride, 10 mM manganese chloride, and 200 μM UDP-4F-Gal. The mixture was allowed to react at 25° C. for 24 hours. A similar mixture containing UDP-Gal instead of UDP-4F-Gal was also allowed to react as a control reaction.

[F6]

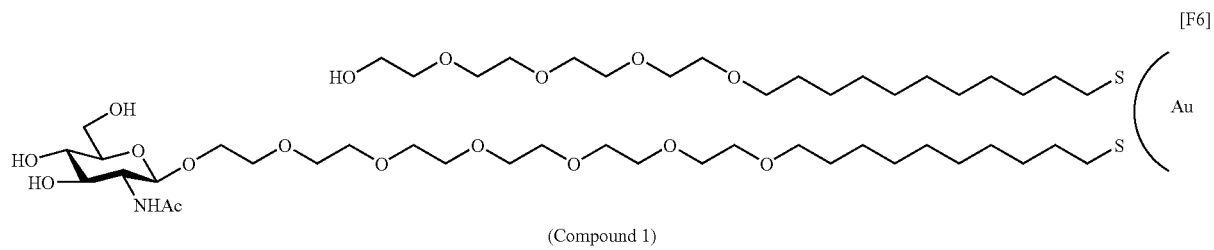

(Compound 1)

After completion of reaction, an aliquot (1 μL) was sampled from the reaction mixture and analyzed by means of an MALDI-TOF-MS (Ultraflex, product of Bruker). In addition to an [M+Na]$^+$ peak (m/z 1059.297) attributed to compound 2 (starting material), an [M+Na]$^+$ peak (m/z 1223.457) attributed to a 4F-galactose adduct was detected, thereby confirming formation of a sugar chain containing 4F-galactosylβ1-4N-acetylglucosamine (compound 3). In the reaction employing UDP-Gal, an [M+Na]$^+$ peak (m/z 1221.476) attributed to a sugar chain containing galactosylβ1-4N-acetylglucosamine (compound 4) was detected.

[F7]

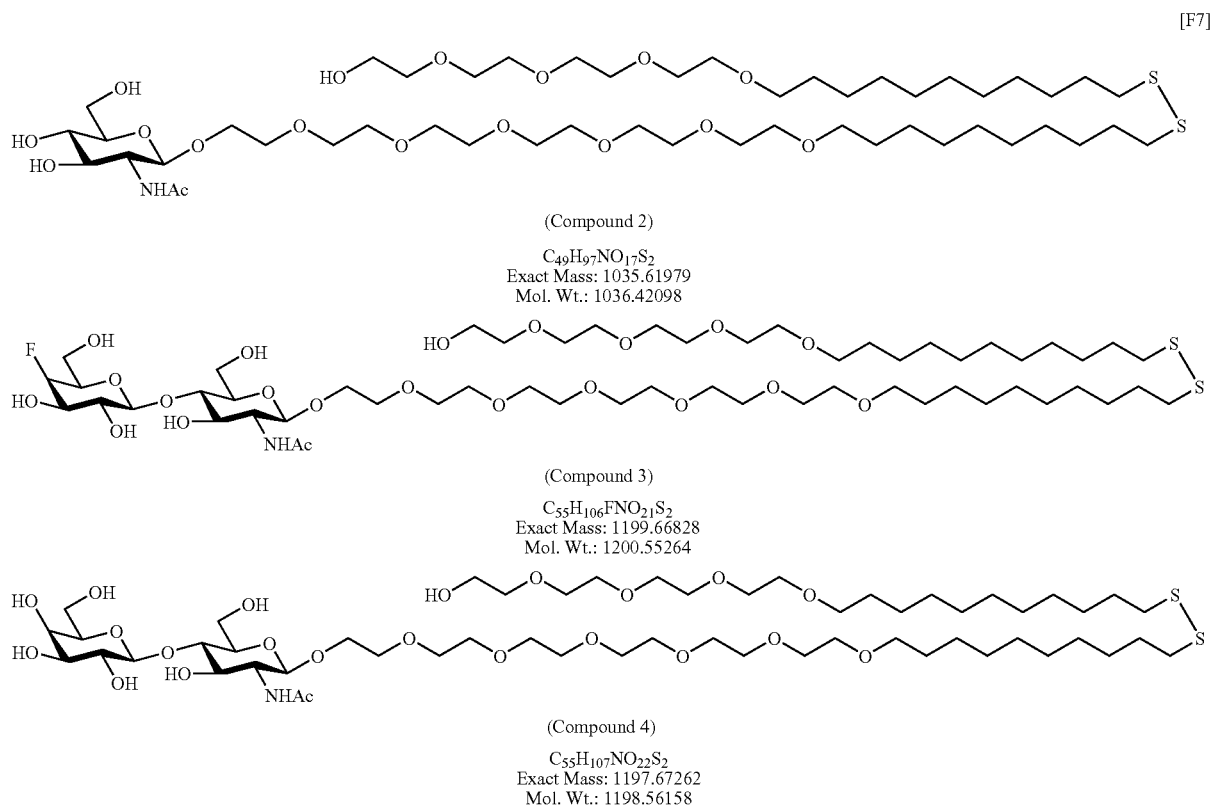

(Compound 2)

$C_{49}H_{97}NO_{17}S_2$
Exact Mass: 1035.61979
Mol. Wt.: 1036.42098

(Compound 3)

$C_{55}H_{106}FNO_{21}S_2$
Exact Mass: 1199.66828
Mol. Wt.: 1200.55264

(Compound 4)

$C_{55}H_{107}NO_{22}S_2$
Exact Mass: 1197.67262
Mol. Wt.: 1198.56158

Referential Example 2

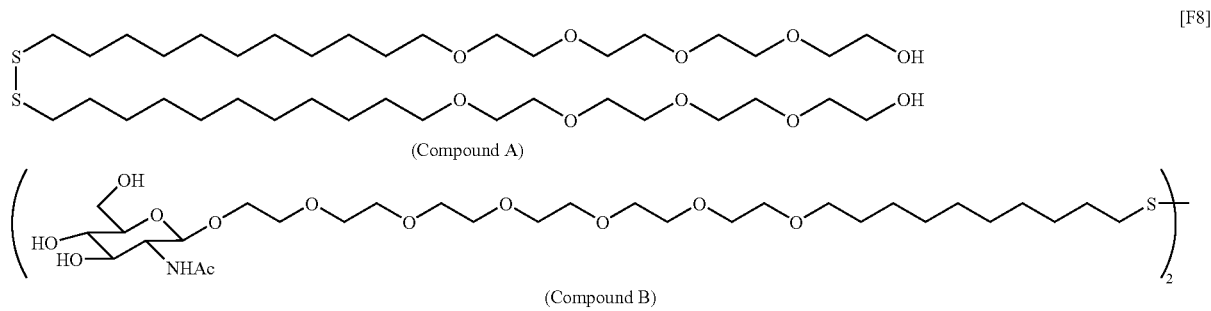

(Compound A)

(Compound B)

Compound A synthesized through a method by S. Penades et al. (Chemistry, A European Journal, (2003), 9, 1909-1921) mg, 69 μmol) and compound B, which is a similar compound having at each end N-acetylglucosamine (10 mg, 7.6 μmol) were dissolved in a methanol (35 mL)-distilled water (5 mL) solvent mixture, and tetrachloroauric acid (25.5 mg, 75 μmol) was added to the solution. An aqueous sodium borohydride solution (70 mg/5 mL) was added portionwise to the resultant solution, followed by stirring at room temperature for 12 hours. The formed microparticles were purified by means of a centrifugal ultrafiltration apparatus employing Centriplus YM-50 (product of Millipore). The purified microparticles were dissolved in distilled water, and the solution was subjected to mass analysis by means of a MALDI-TOF Mass employing as a matrix 2,5-dihydroxybenzoic acid (DHB).

Through mass analysis, a molecular weight peak ([M+Na]$^+$ m/z 1058.389) attributed to a heterodisulfide form of compound A and compound B was observed, thereby confirming synthesis of compound 1 immobilized on gold microparticles by the mediation of a thiol-group-containing spacer.

Example 3

Enzymatic α2,3-sialyltransfer Reaction to a Sugar Chain Containing 4F-galactose The medium of each of the reaction-completed mixtures was substituted by distilled water by means of a centrifugal ultrafiltration unit (Microcon YM☐10, product of Millipore). On the same scale as employed in the aforementioned β1,4-galactose transfer reaction (about 50 μM sugar chain included), rat-derived α2,3-(N)-sialyltransferase (74 munits/mL-reaction mixture) (product of Calbiochem) was added to a 10 mM HEPES-NaOH buffer (pH 7.5) containing 100 mM sodium chloride, 10 mM manganese chloride, and 400 μM CMP-N-acetylneuraminic acid (CMP-NeuAc), and the resultant mixture was allowed to react at 25° C. for 24 hours.

Twenty-four hours after initiation of reaction, the medium of the reaction system was substituted by distilled water by means of Microcon YM-10, followed by drying under reduced pressure. In order to separate sugar chain moieties from gold microparticles, the dried product was dissolved in a 1 mM iodine in methanol, followed by stirring at room temperature for about two hours. The product was dried again under reduced pressure, to thereby completely remove the iodine solution, and the dried product was sufficiently suspended in 10% methanol. The suspension was centrifuged (20,000×g, 10 min), to thereby remove gold microparticles fractions. The thus-produced supernatant was employed as a sample for the analysis by means of a MALDI-TOF-MS (Ultraflex, product of Bruker).

Through mass analysis, in the reaction employing a sugar chain containing galactosylβ1-4N-acetylglucosamine, peaks [M+Na]$^+$ (m/z 1512.629) and [M$^+$ 2Na–H]$^+$ (m/z 1534.626) attributed to compound 5, which is a sialyltransfer compound, were detected, whereas, in the reaction employing a sugar chain containing 4F-galactosylβ1-4N-acetylglucosamine, peaks [M+Na]$^+$ (m/z 1514) and [M$^+$ 2Na–H]$^+$ (m/z 1536) attributed to compound 6, which would be detected as a result of sialyltransfer, were not detected. Therefore, at least enzymatic α2,3-sialylation was found to be inhibited by the sugar chain containing 4F-galactose.

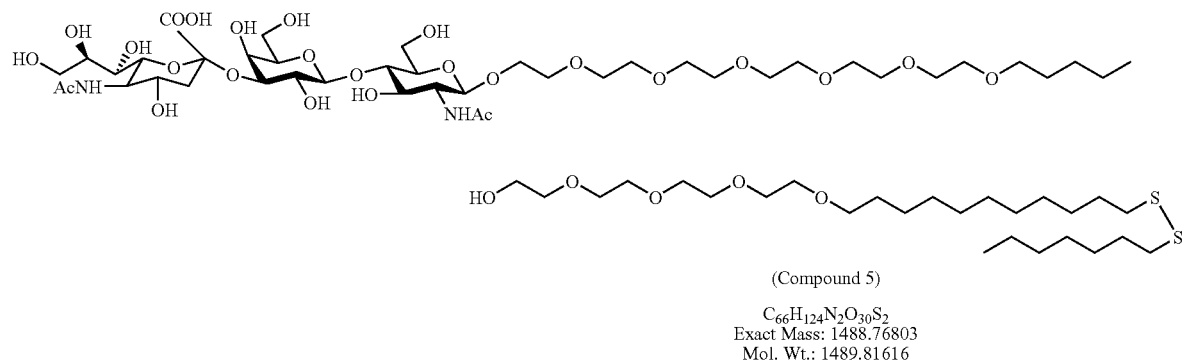

(Compound 5)

$C_{66}H_{124}N_2O_{30}S_2$
Exact Mass: 1488.76803
Mol. Wt.: 1489.81616

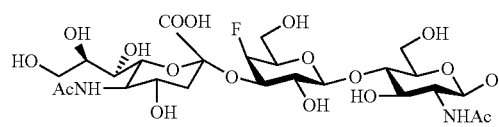
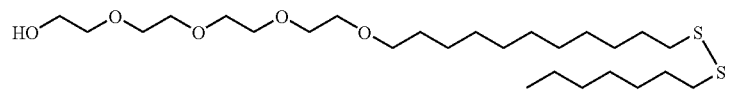

(Compound 6)

$C_{66}H_{123}FN_2O_{29}S_2$
Exact Mass: 1490.7637
Mol. Wt.: 1491.80722

Example 4

Synthesis of 4-methylumbelliferyl 4F—N-acetyllactosamine (4MU-4F-LacNAc)

4F-Galactose transfer reaction to 4MU-GlcNAc (compound 7, product of Sigma) serving as an acceptor was performed in the presence of β1,4-galactosyltransferase. Specifically, human-derived β1,4-galactosyltransferase (product of Toyobo) (200 mU/mL-reaction mixture) was added to a 10 mM HEPES-NaOH (pH 7.5) buffer containing 10 mM manganese chloride, 100 mM sodium chloride, 50 mU/mL-reaction mixture alkaline phosphatase, 20 μM PA (pyridylaminated) chitobiose, and 2.35 μM UDP-4F-Gal, and the mixture was allowed to react at 25° C. A similar mixture employing 50 μM UDP-Gal was also allowed to react as a control reaction.

Twenty-four hours after initiation of the reaction, the reaction was stopped through heat treatment at 90° C. for five minutes. After dilution, the reaction mixture was analyzed through high-performance liquid chromatography (HPLC). In the analysis, separation was performed by means of an ODS-3 column (product of GL science) with 10% acetonitrile as an eluent. Detection was performed by means of a fluoresce spectrometer (excitation wavelength: 325 nm, fluorescence wavelength: 372 nm). A fraction corresponding to a peak newly observed as a result of β1,4-galactosyltransferase reaction was collected and dried under reduced pressure. The dried product was subjected to mass analysis by means of a MALDI-TOF-MS employing DHB as a matrix. Mass analysis detected an [M+Na]⁺ peak (m/z 565.90) attributed to compound 8, thereby confirming formation of a sugar chain containing 4F-galactose; i.e., 4MU-4F-LacNAc (compound 8). The amount of formed 4MU-4F-LacNAc was determined to be 1.34 μM from an area ratio obtained in HPLC.

Notably, in the control reaction employing UDP-Gal, an [M+Na]⁺ peak (m/z 563.89) attributed to compound 9 was also detected in MALDI-TOF-MS, thereby confirming formation of 20 μM of 4MU-LacNAc (compound 9).

[F10]

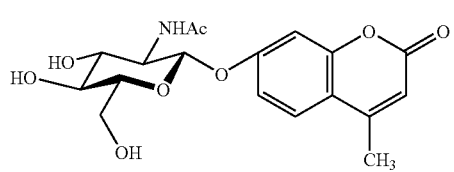

(Compound 7)

$C_{18}H_{21}NO_8$
Exact Mass: 379.12672
Mol. Wt.: 379.36124

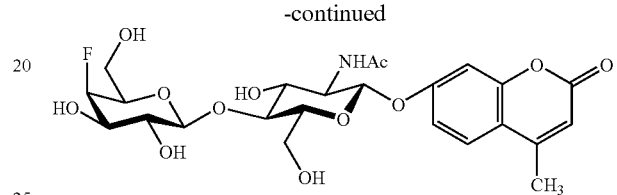

(Compound 8)

$C_{24}H_{30}FNO_{12}$
Exact Mass: 543.1752
Mol. Wt.: 543.4929

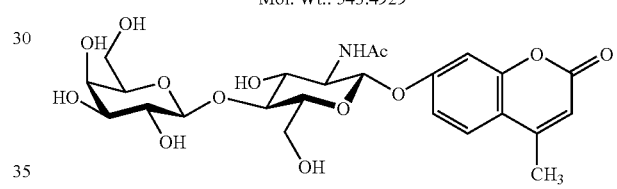

(Compound 9)

$C_{24}H_{31}NO_{13}$
Exact Mass: 541.17954
Mol. Wt.: 541.50184

(2) Mass-Production of 4MU-4F-LacNAc (Compound 8) and 4MU-LacNAc (Compound 9)

Human-derived β1,4-galactosyltransferase (200 mU/mL-reaction mixture) was added to a 10 mM HEPES-NaOH buffer (pH 7.5) containing 10 mM manganese chloride, 100 mM sodium chloride, 50 mU/mL-reaction mixture alkaline phosphatase, 40 μM 4MU-GlcNAc, and 55 μM UDP-4F-Gal, and the mixture was allowed to react at 25° C.

One hundred forty hours after initiation of the reaction, the reaction mixture was treated at 90° C. for 10 minutes, followed by centrifugation at 20,000 g for 10 minutes. The supernatant collected through centrifugation was concentrated through drying under reduced pressure, and a fraction of a target peak was collected by means of an ODS-3 column. The fraction was dried under reduced pressure, and the dried product was dissolved again in distilled water. Insoluble matter was removed from the solution by means of Ultrafree MC 0.22 μm (product of Millipore), and the solution was dried again under reduced pressure. The dried product was dissolved again in distilled water, which was employed as 4MU-4F-LacNAc in the subsequent experiments.

Separately, human-derived β1,4-galactosyltransferase (40 mU/mL-reaction mixture) was added to a 10 mM HEPES-NaOH buffer (pH 7.5) containing 10 mM manganese chloride, 100 mM sodium chloride, 50 mU/mL-reaction mixture alkaline phosphatase, 100 μM 4MU-GlcNAc, and 200 μM UDP-Gal, and the mixture was allowed to react at 25° C. for 48 hours, to thereby prepare 4MU-LacNAc in a similar manner.

(3) Enzymatic α2,3-sialyltransfer Reaction to 4MU-4F-LacNAc (Compound 8)

To a 10 mM HEPES-NaOH buffer (pH 7.5) containing 10 mM manganese chloride, 100 mM sodium chloride, 200 µM CMP-NeuAc, 50 mU/mL-reaction mixture alkaline phosphatase, and 20 µM 4MU-4F-LacNAc, rat-derived α2,3-N-sialyltransferase (product of Calbiochem) (92.5 mU/mL-reaction mixture) was added, and the mixture was allowed to react at 25° C. In a similar manner, a similar mixture employing 4MU-LacNAc as an acceptor was allowed to react as a control reaction.

An aliquot was sampled from the reaction mixture at hour 1, hour 4, hour 10, and hour 24 after initiation of the reaction. Finally, the reaction was terminated through addition of 80% acetonitrile (4 times in volume) and vigorous stirring. The reaction mixture was diluted with distilled water, and the diluted product was analyzed through HPLC employing an ODS-3 column and 10% acetonitrile-20 mM ammonium formate serving as an eluent. Through HPLC analysis, a new peak, which was attributed to the action of α2,3-N-sialyltransferase, was observed in each case. A fraction corresponding to each peak was collected and dried under reduced pressure. The dried product was subjected to MALDI-TOF-MS employing DHB as a matrix. Mass analysis detected, in the reaction employing 4MU-4F-LacNAc, an [M+H]$^+$ peak (m/z 835.13), thereby confirming formation of compound 10. Also, in the reaction employing 4MU-LacNAc, an [M+H]$^+$ peak (m/z 833.02) was detected, thereby confirming formation of compound 11.

was added. The concentration of 4MU-4F-LacNAc was adjusted to 20, 40, 80, or 150 µM. The mixture was allowed to react at 25° C.

Precisely 60 minutes after initiation of the reaction, the reaction was terminated through addition of 80% acetonitrile (4 times in volume) and vigorous stirring. The reaction mixture was diluted, and the diluted product was analyzed through HPLC. The enzymatic activity was calculated at each 4MU-4F-LacNAc concentration, and through 1/[S]-1/v plotting, $K_m$ and $V_{max}$ of α2,3-sialyltransferase with respect to 4MU-4F-LacNAc were determined to be 188 µM and 12.60 nmol/min/mg, respectively. Note that "1U" was defined as an enzyme amount which realizes sialylated sugar to form in an amount of 1 µmol/min under the above conditions.

Separately, to 10 mM HEPES-NaOH buffer (pH 7.5) containing 4MU-LacNAc, 10 mM manganese chloride, 100 mM sodium chloride, 50 mU/mL-reaction mixture alkaline phosphatase, and 200 µM CMP-NeuAc, rat-derived α2,3-sialyltransferase (37 mU/mL-reaction mixture) was added. The concentration of 4MU-LacNAc was adjusted to 20, 40, 80, or 150 µM. The mixture was allowed to react at 25° C. for eight minutes. The enzymatic activity was calculated at each 4MU-LacNAc concentration determined through HPLC, and through 1/[S]-1/v plotting, $K_m$ and $V_{max}$ of α2,3-sialyltransferase with respect to 4MU-LacNAc were determined to be 129 µM and 146.9 nmol/min/mg, respectively.

The results are shown in Table 2. As shown in Table 2, the catalytic efficiency of rat-derived α2,3-sialyltransferase with respect to 4MU-4F-LacNAc, which is a sugar chain containing 4F-galactose, is 6% or lower than that determined with respect to 4MU-LacNAc, indicating that 4MU-4F-LacNAc is a useful transferase inhibitor.

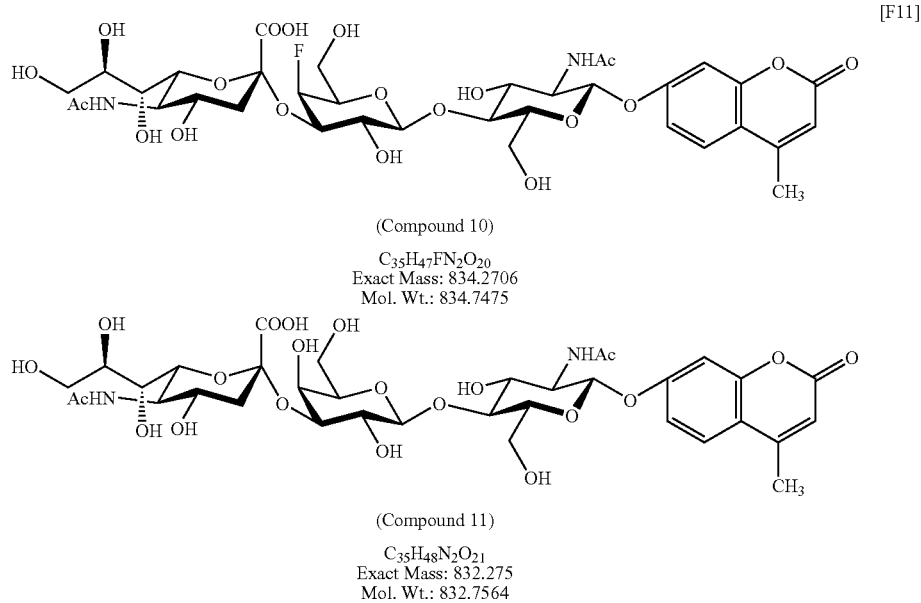

[F11]

(Compound 10)
C$_{35}$H$_{47}$FN$_2$O$_{20}$
Exact Mass: 834.2706
Mol. Wt.: 834.7475

(Compound 11)
C$_{35}$H$_{48}$N$_2$O$_{21}$
Exact Mass: 832.275
Mol. Wt.: 832.7564

(4) Kinetic Analysis of α2,3-sialyltransfer Reaction to 4MU-4F-LacNAc

To 10 mM HEPES-NaOH buffer (pH 7.5) containing 4MU-4F-LacNAc, 10 mM manganese chloride, 100 mM sodium chloride, 50 mU/mL-reaction mixture alkaline phosphatase, and 200 µM CMP-NeuAc, rat-derived α2,3-N-sialyltransferase (Calbiochem) (74 mU/mL-reaction mixture)

TABLE 2

| | | | | |
|---|---|---|---|---|
| 4MU-4F-LacNAc (µM) | 20 | 40 | 80 | 150 |
| Activity (mU/mL) | 0.9972 | 1.756 | 3.214 | 4.541 |
| 4MU-LacNAc (µM) | 20 | 40 | 80 | 150 |
| Activity (mU/mL) | 16.20 | 28.50 | 45.36 | 66.23 |

(5) Enzymatic α2,6-sialyltransfer Reaction to 4MU-4F-LacNAc

To a 10 mM HEPES-NaOH buffer (pH 7.5) containing 10 mM manganese chloride, 100 mM sodium chloride, 200 μM CMP-NeuAc, 50 mU/mL-reaction mixture alkaline phosphatase, and 20 μM 4MU-4F-LacNAc, rat-derived α2,6-N-sialyltransferase (product of Calbiochem) (10 mU/mL-reaction mixture) was added, and the mixture was allowed to react at 25° C. In a similar manner a similar mixture employing 4MU-LacNAc as an acceptor was allowed to react as a control reaction.

An aliquot was sampled from the reaction mixture at hour 1, hour 4, hour 10, and hour 24 after initiation of the reaction. Finally, the reaction was terminated through addition of 80% acetonitrile (4 times in volume) and vigorous stirring. The reaction mixture was diluted with distilled water, and the diluted product was analyzed through HPLC employing an ODS-3 column and 10% acetonitrile-20 mM ammonium formate serving as an eluent. Through HPLC analysis, a new peak, which was attributed to enzymatic α2,6-N-sialyltransfer reaction, was observed in each case. A fraction corresponding to each peak was collected and dried under reduced pressure. The dried product was subjected to MALDI-TOF-MS employing DHB as a matrix. Mass analysis detected, in the reaction employing 4MU-4F-LacNAc, an [M+Na]$^+$ peak (m/z 856.88), thereby confirming formation of compound 12. Also, in the reaction employing 4MU-LacNAc, an [M+Na]$^+$ peak (m/z 855.06) was detected, thereby confirming formation of compound 13.

(6) Kinetic Analysis of α2,6-sialyltransfer Reaction to 4MU-4F-LacNAc

To 10 mM HEPES-NaOH buffer (pH 7.5) containing 4MU-4F-LacNAc, 10 mM manganese chloride, 100 mM sodium chloride, 50 mU/mL-reaction mixture alkaline phosphatase, and 200 μM CMP-NeuAc, rat-derived α2,6-N-sialyltransferase (Calbiochem) (40 mU/mL-reaction mixture) was added. The concentration of 4MU-4F-LacNAc was adjusted to 20, 40, 80, 120, or 150 μM. The mixture was allowed to react at 25° C.

Precisely 120 minutes after initiation of the reaction, the reaction was terminated through addition of 1M NaOH (⅕ times in volume). The reaction mixture was neutralized and diluted with an HPLC eluent, and the diluted product was analyzed through HPLC. The enzymatic activity was calculated at each 4MU-4F-LacNAc concentration, and through $1/[S]-1/v$ plotting, the relationship $1/v=260.27/[S]-0.1005$ was obtained. Thus, $K_m$ and $V_{max}$ could not be calculated. Note that "1U" was defined as an enzyme amount which realizes formation of sialylated sugar in an amount of 1 μmol/min under the above conditions.

Separately, to 10 mM HEPES-NaOH buffer (pH 7.5) containing 4MU-LacNAc, 10 mM manganese chloride, 100 mM sodium chloride, 50 mU/mL-reaction mixture alkaline phosphatase, and 200 μM CMP-NeuAc, rat-derived α2,6-sialyltransferase (40 mU/mL-reaction mixture) was added. The concentration of 4MU-LacNAc was adjusted to 20, 40, 80, 120, or 150 μM. The mixture was allowed to react at 25° C. for 10 minutes. The enzymatic activity was calculated at each

[F12]

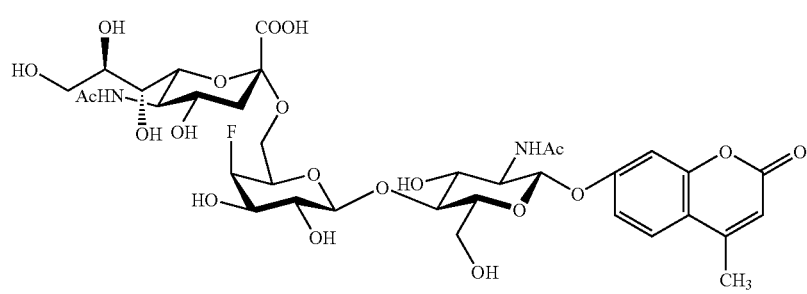

(Compound 12)
$C_{35}H_{47}FN_2O_{20}$
Exact Mass: 834.2706
Mol. Wt.: 834.7475

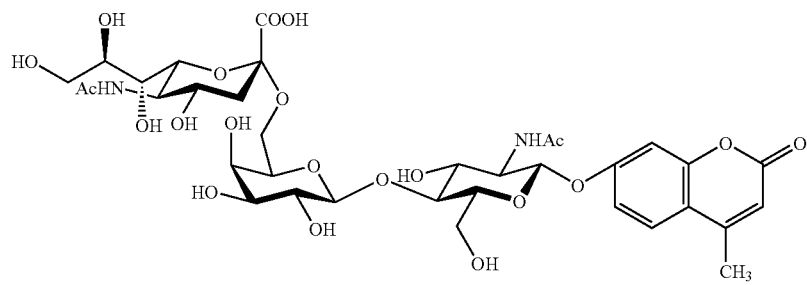

(Compound 13)
$C_{35}H_{48}N_2O_{21}$
Exact Mass: 832.275
Mol. Wt.: 832.7564

4MU-LacNAc concentration determined through HPLC, and through 1/[S]-1/v plotting, $K_m$ and $V_{max}$ of α2,3-sialyltransferase with respect to 4MU-LacNAc were determined to be 217 μM and 65.24 nmol/min/mg.

The enzymatic activity values at respective concentrations are compared. As shown in Table 3, the sialyltransferase activity of rat-derived α2,6-sialyltransferase with respect to 4MU-4F-LacNAc, which is a sugar chain containing 4F-galactose, is clearly decreased, indicating that 4MU-4F-LacNAc is a useful transferase inhibitor.

TABLE 3

|  | 20 | 40 | 80 | 120 | 150 |
|---|---|---|---|---|---|
| 4MU-4F-LacNAc (μM) | | | | | |
| Activity (mU/mL) | 0.07743 | 0.1561 | 0.3223 | 0.4596 | 0.6348 |
| 4MU-LacNAc (μM) | | | | | |
| Activity (mU/mL) | 0.8800 | 1.667 | 2.504 | 3.734 | 4.828 |

Example 5

Synthesis of Pyridylaminated Galactosylchitobiose (1) Synthesis of pyridylaminated 4F-galactosylchitobiose Chitobiose (GlcNAcβ1-4GlcNAc, product of Sigma) was pyridylaminated (PA) through a known method (Hase et al., J. Biochem., 95, 197-203 (1984)), and a purified product thereof was collected through gel filtration and lyophilization (compound 14). 4F-Galactose transfer reaction to compound 14 serving as an acceptor was performed in the presence of □1,4-galactosyltransferase. Specifically, human-derived □1,4-galactosyltransferase (product of Toyobo) (160 mU/mL-reaction mixture) was added to a 10 mM HEPES-NaOH (pH 7.5) buffer containing 10 mM manganese chloride, 100 mM sodium chloride, 25 μM PA (pyridylaminated) chitobiose, and 4.7 μM UDP-4F-Gal, and the mixture was allowed to react at 25° C. A similar mixture employing 100 μM UDP-Gal was also allowed to react as a control reaction.

Ten hours after initiation of the reaction, the reaction was stopped through heat treatment at 90° C. for five minutes. After dilution with distilled water, the reaction mixture was analyzed through high-performance liquid chromatography (HPLC). In the analysis, separation was performed by means of a Develosil C30-UG-5 column (product of Nomura Chemical Co., Ltd.) with 10 mM sodium phosphate (pH 3.8) and a mixture of 10 mM sodium phosphate (pH 3.8) and 0.5% (w/v) 1-butanol as eluents, with concentrations of the eluents being graded. A fraction corresponding to a peak newly observed as a result of reaction was collected and dried under reduced pressure for concentration. After salt-removal by use of ZipTipc$_{C18}$, the adsorbed fraction was subjected to mass analysis by means of a MALDI-TOF-MS (Ultraflex, product of Bruker) employing DHB as a matrix. Mass analysis detected an [M+Na]$^+$ peak (m/z 690.02) attributed to compound 15, thereby confirming formation of a 4F-galactosylated sugar. From an area ratio obtained in HPLC, formation of 3.80 μM of pyridylaminated (PA) 4F-galactosylated chitobiose (compound 15) was confirmed. In the control reaction employing UDP-Gal, an [M+Na]$^+$ peak (m/z 687.56) attributed to compound 16 was detected in the analysis by means of a MALDI-TOF-MS, and formation of 23.5 μM of pyridylaminated (PA) 4F-galactosylchitobiose (compound 16) was confirmed.

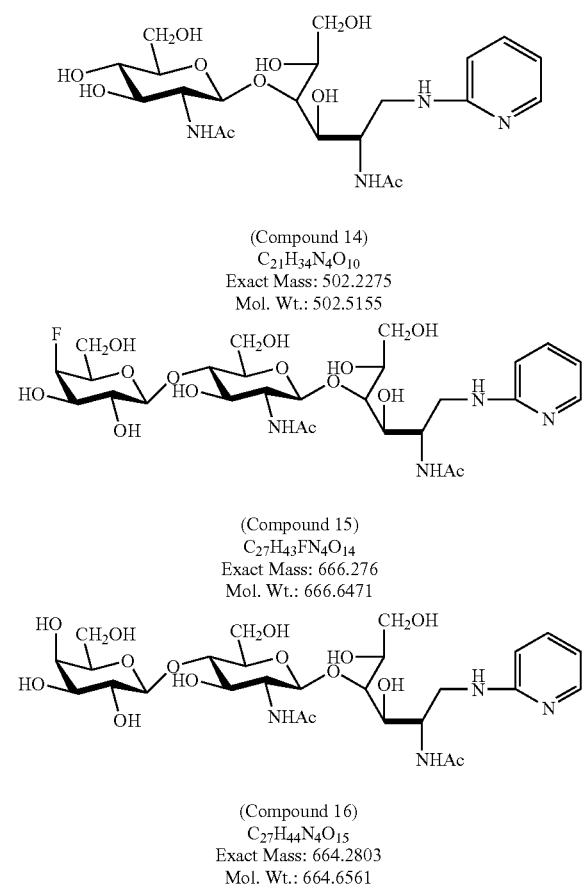

[F13]

(Compound 14)
C$_{21}$H$_{34}$N$_4$O$_{10}$
Exact Mass: 502.2275
Mol. Wt.: 502.5155

(Compound 15)
C$_{27}$H$_{43}$FN$_4$O$_{14}$
Exact Mass: 666.276
Mol. Wt.: 666.6471

(Compound 16)
C$_{27}$H$_{44}$N$_4$O$_{15}$
Exact Mass: 664.2803
Mol. Wt.: 664.6561

(2) Mass-Production of pyridylaminated (PA) 4F-galactosylchitobiose (compound 15) and pyridylaminated (PA) galactosylchtiobiose (Compound 16)

Human-derived β1,4-galactosyltransferase (200 mU/mL-reaction mixture) was added to a 10 mM HEPES-NaOH buffer (pH 7.5) containing 10 mM manganese chloride, 100 mM sodium chloride, 25 μM PA chitobiose, and 2.35 μM UDP-4F-Gal, and the mixture was allowed to react at 25° C.

Thirty-six hours after initiation of the reaction, the reaction mixture was treated at 90° C. for 5 minutes and concentrated through drying under reduced pressure. A fraction of a target peak was collected by means of a Develosil C30-UG-5 column. The fraction was dried under reduced pressure, and the dried product was subjected to salt-removal treatment by means of a TSKgel-Oligo-PW column (product of Tosoh) equilibrated with 20 mM ammonium hydrogencarbonate. After collection of a fraction of the target peak, the fraction was dried under reduced pressure, and the dried product was dissolved again in distilled water. The solution was employed as pyridylaminated (PA) 4F-galactosylchitobiose (compound 15) in the subsequent experiments.

Separately, in a similar manner, human-derived β1,4-galactosyltransferase (200 mU/mL-reaction mixture) was added to a 10 mM HEPES-NaOH buffer (pH 7.5) containing 10 mM manganese chloride, 100 mM sodium chloride, 25 μM pyridylaminated (PA) chitobiose, and 50 μM UDP-Gal, and the mixture was allowed to react at 25° C. for eight hours, to thereby prepare pyridylaminated (PA) galactosylchitobiose (compound 16).

(3) Enzymatic α2,3-sialyltransfer Reaction to pyridylaminated (PA) 4F-galactosylchitobiose To a 10 mM HEPES-NaOH buffer (pH 7.5) containing 10 mM manganese chloride, 100 mM sodium chloride, 100 μM CMP-NeuAc, 0.02% (w/v) BSA, and 10 μM pyridylaminated (PA) 4F-galactosylated chitobiose, rat-derived α2,3-N-sialyltransferase (product of Calbiochem) (100 mU/mL-reaction mixture) was added, and the mixture was allowed to react at 25° C. In a similar manner, a similar mixture employing pyridylaminated (PA) galactosylated chitobiose as an acceptor was allowed to react as a control reaction.

An aliquot was sampled from the reaction mixture at hour 2.5 and hour 24 after initiation of the reaction. Finally, the reaction was terminated through addition of 10 mM sodium phosphate (pH 4.3) (9 times in volume) and vigorous stirring. The product was analyzed through HPLC employing a C30-UG-5 column. Through HPLC analysis, a new peak, which was attributed to the reaction by use of α2,3-N-sialyltransferase, was observed in each case. A fraction corresponding to each peak was collected and dried under reduced pressure. By means of a TSKgel-Oligo-PW column (product of Tosoh) equilibrated with 20 mM ammonium hydrogencarbonate, a fraction of the target peak was collected and dried under reduced pressure. The dried product was subjected to MALDI-TOF-MS employing DHB as a matrix. Mass analysis detected, in the reaction employing pyridylaminated (PA) 4F-galactosylchitobiose, an $[M+H]^+$ peak (m/z 959.45), thereby confirming formation of compound 17. Also, in the reaction employing pyridylaminated (PA) galactosyl chitobiose, an $[M+H]^+$ peak (m/z 957.31) was detected, thereby confirming formation of compound 18.

Percent conversion values to the two compounds were compared with each other on the basis of the peak area obtained in HPLC. In the reaction employing pyridylaminated (PA) 4F-galactosylchitobiose as an acceptor, reactivity of α2,3-sialyltransferase has been found to considerably decrease, indicating that pyridylaminated (PA) 4F-galactosylchitobiose is a useful inhibitor.

(4) Enzymatic α2,6-sialyltransfer Reaction to pyridylaminated (PA) 4F-galactosylchitobiose To a 10 mM HEPES-NaOH buffer (pH 7.5) containing 10 mM manganese chloride, 100 mM sodium chloride, 100 μM CMP-NeuAc, 0.02% (w/v) BSA, and 10 μM pyridylaminated (PA) 4F-galactosylated chitobiose, rat-derived α2,6-N-sialyltransferase (product of Calbiochem) (40 mU/mL-reaction mixture) was added, and the mixture was allowed to react at 25° C. In a similar manner, a similar mixture employing pyridylaminated (PA) galactosylated chitobiose as an acceptor was allowed to react as a control reaction.

An aliquot was sampled from the reaction mixture at hour 1, hour 2.5, hour 8, and hour 24 after initiation of the reaction. Finally, the reaction was terminated through addition of a mixture of 0.5M triethylamine-acetic acid (pH 7.3) and acetonitrile (25:75) (19 times in volume) and vigorous stirring. The product was analyzed through HPLC. In HPLC, separation was performed by means of an Amide-80 column (product of Tosoh) and, as eluents, a mixture of 10 mM triethylamine-acetic acid (pH 7.3) and acetonitrile (25:75) and a mixture of 0.5M triethylamine-acetic acid (pH 7.3) and acetonitrile (25:75) with concentrations of the eluents being graded were employed. Through HPLC analysis, a new peak, which was attributed to the reaction, was observed in each case. A fraction corresponding to each peak was collected and dried under reduced pressure. The dried product was subjected to MALDI-TOF-MS employing DHB as a matrix. Mass analysis detected an $[M+H]^+$ peak (m/z 659.74) attributed to compound 19, thereby confirming formation of compound 19. Also, in the control reaction employing UDP-Gal, an $[M+H]^+$ peak (m/z 657.74) attributed to compound 20 was detected through MALDI-TOF-MS, confirming formation of compound 20.

Percent conversion values to the two compounds were compared with each other on the basis of the peak area obtained in HPLC. In the reaction employing pyridylaminated (PA) 4F-galactosylchitobiose as an acceptor, reactivity

[F14]

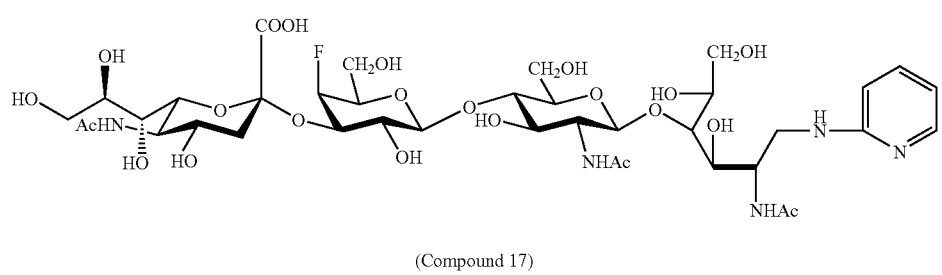

(Compound 17)
$C_{38}H_{60}FN_5O_{22}$
Exact Mass: 957.3714
Mol. Wt.: 957.9017

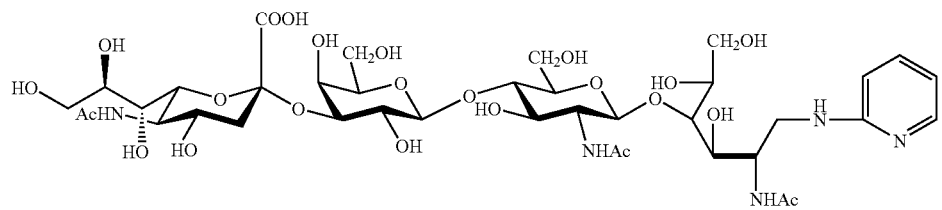

(Compound 18)
$C_{38}H_{61}N_5O_{23}$
Exact Mass: 955.3757
Mol. Wt.: 955.9016 of α2,6-sialyltransferase has been found to considerably decrease, indicating that pyridylaminated (PA) 4F-galactosylchitobiose is a useful inhibitor.

[F15]

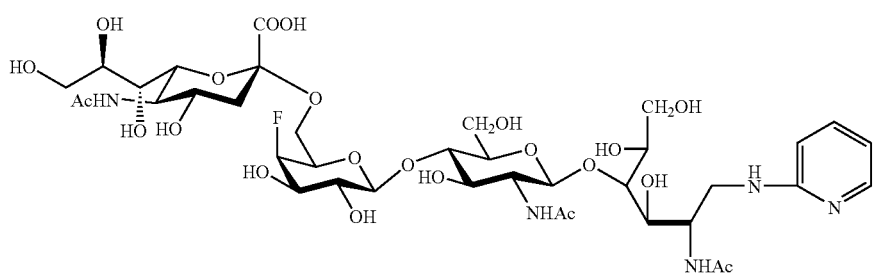

(Compound 19)

$C_{38}H_{60}FN_5O_{22}$
Exact Mass: 957.3714
Mol. Wt.: 957.9017

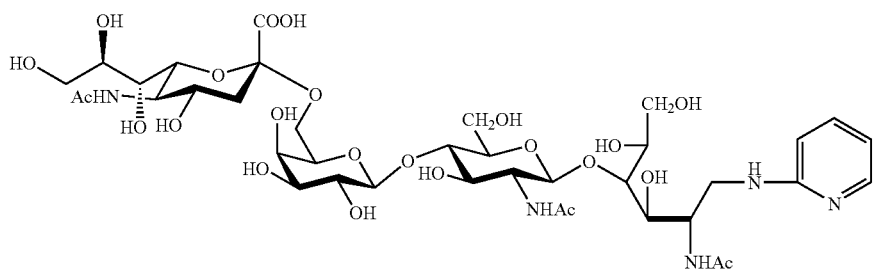

(Compound 20)

$C_{38}H_{61}N_5O_{23}$
Exact Mass: 955.3757
Mol. Wt.: 955.9106

We claim:

1. A method for inhibiting sugar chain elongation in vitro by a glycosyltransferase comprising contacting the glycosyltransferase with an acceptor compound, which is a monosaccharide, oligosaccharide, an oligosaccharide bound to a carrier, or an immobilized saccharide bonded to a carrier, optionally via a spacer, having at the end thereof a 4-position halogenated galactose residue.

2. The method of claim 1, wherein said acceptor compound having at the end thereof a 4-position halogenated galactose residue is represented by formula (I):

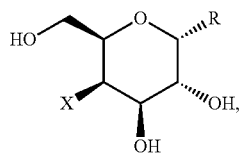

wherein X represents a halogen atom, and R represents a monosaccharide, an oligosaccharide, an oligosaccharide bound to a carrier, or an immobilized saccharide bonded to a carrier, optionally via a spacer.

3. The method of claim 1, wherein said acceptor compound having at the end thereof a 4-position halogenated galactose residue is represented by formula (I'):

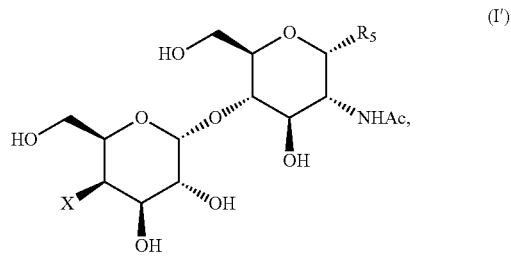

wherein X represents a halogen atom, and $R_5$ represents a hydrogen atom, a hydroxyl group, a monosaccharide, an oligosaccharide, an oligosaccharide bound to a carrier, or an immobilized saccharide bonded to a carrier, optionally via a spacer.

4. A method for producing a second acceptor compound having at an end thereof a 4-position halogenated galactose residue comprising:

contacting a first acceptor compound for a 4-position halogenated galactose residue, which is a monosaccharide, an oligosaccharide, an oligosaccharide bound to a carrier, or an immobilized saccharide bonded to a carrier, optionally via a spacer, with a glycosyltransferase and a sugar donor that is a halogenated galactose sugar nucleotide represented by formula (II):

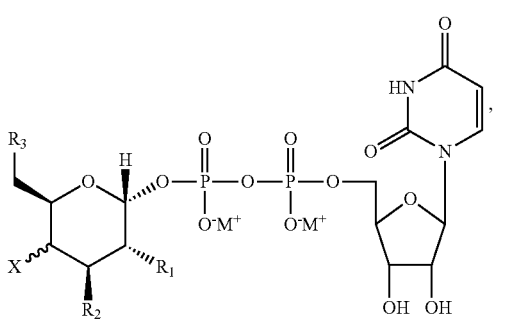

(II)

wherein each of $R_1$ to $R_3$ represents a hydroxyl group, an acetyl group, a halogen atom, or a hydrogen atom; X represents a halogen atom; and $M^+$ represents a hydrogen ion or a metal ion;

wherein said glycosyltransferase is selected from the group consisting of a β1,4-galactosyltransferase, a β1,3-galactosyltransferase, and an α-1,3-galactosyltransferase; or another galactosyltransferase that transfers a 4-deoxy-4-halogeno-galactosyl group to said sugar donor.

5. The method of claim 4, wherein $R_1$, $R_2$ and $R_3$ in formula (II) are each a hydroxyl group and X is a fluorine atom.

6. The method of claim 4, wherein at least one of $R_1$, $R_2$ and $R_3$ in formula (II) is an acetyl group, a halogen atom, or a hydrogen atom.

7. The method of claim 4, wherein at least one of $R_1$, $R_2$ and $R_3$ in formula (II) is a halogen atom.

8. The method of claim 4, wherein at least one of $R_1$, $R_2$ and $R_3$ in formula (II) is a hydrogen atom.

9. The method of claim 4, wherein said second acceptor compound has at the end thereof a 4-position halogenated galactose residue represented by formula (I):

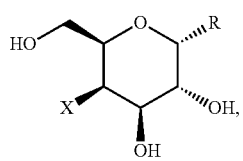

(I)

wherein X represents a halogen atom, and R represents a monosaccharide, an oligosaccharide, an oligosaccharide bound to a carrier, or an immobilized saccharide bonded to a carrier, optionally via a spacer.

10. The method of claim 4, wherein said second acceptor compound having at the end thereof a 4-position halogenated galactose residue is represented by formula (I'):

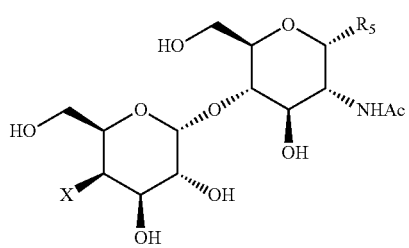

(I')

wherein X represents a halogen atom, and $R_5$ represents a hydrogen atom, a hydroxyl group, a monosaccharide, an oligosaccharide, an oligosaccharide bound to a carrier, or an immobilized saccharide bonded to a carrier, optionally via a spacer.

11. A method for producing a 4-position halogenated galactose sugar nucleotide (II), comprising:

phosphorylating a compound represented by formula (III) by contacting it with phosphate ion in the presence of a bacterial galactokinase, thus forming a compound represented by formula (IV), and contacting the compound represented by formula (IV) and a uridine sugar nucleotide with a bacterial hexose-1-phosphate uridylyltransferase, thus synthesizing a compound represented by formula (II); wherein formulas (II), (III) and (IV) are:

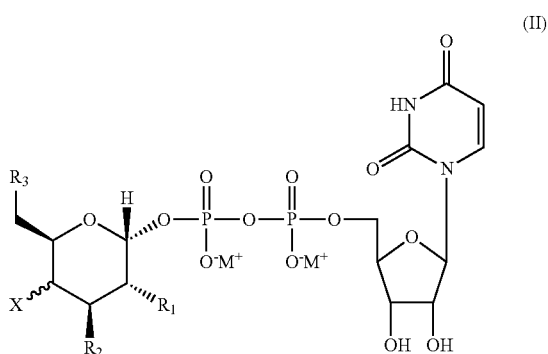

(II)

(III)

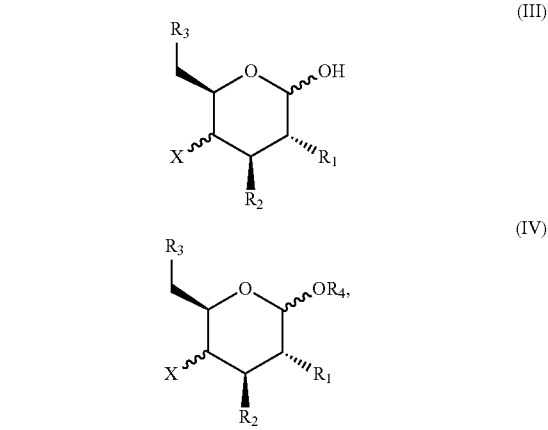

(IV)

wherein each of $R_1$ to $R_3$ represents a hydroxyl group, an acetyl group, a halogen atom, or a hydrogen atom; $R_4$ represents a phosphate residue or a salt thereof; X represents a halogen atom; and $M^+$ represents a hydrogen ion or a metal ion.

12. The method of claim 11, wherein each of $R_1$ to $R_3$ in formula (II) is a hydroxyl group and X is a fluorine atom.

13. The method of claim 11, wherein the uridine sugar nucleotide is uridine 5'-diphosphate-glucose.

14. The method of claim 11, wherein the bacterial galactokinase and bacterial hexose-1-phosphate uridylyltransferase are from *Escherichia coli*.

* * * * *